United States Patent [19]

Galantay et al.

[11] 3,961,053

[45] *June 1, 1976

[54] SUBSTITUTED CARBINOL DERIVATIVES

[75] Inventors: Eugene E. Galantay, Liestal, Switzerland; Dietmar A. Habeck, Heidelberg, Germany

[73] Assignee: Sandoz, Inc., E. Hanover, N.J.

[ * ] Notice: The portion of the term of this subsequent to Mar. 6, 1990, has been disclaimed.

[22] Filed: Nov. 18, 1974

[21] Appl. No.: 524,620

Related U.S. Application Data

[60] Continuation of Ser. No. 358,345, May 8, 1973, abandoned, which is a continuation-in-part of Ser. No. 314,833, Dec. 13, 1972, abandoned, which is a division of Ser. No. 71,279, Sept. 10, 1970, Pat. No. 3,719,670, which is a continuation-in-part of Ser. No. 778,777, Nov. 25, 1968, abandoned.

[52] U.S. Cl................................ 424/243; 260/397.4

[51] Int. Cl.$^2$............................................. C07J 1/00
[58] Field of Search................ 424/243; 260/397.4, 260/397.45

[56] References Cited
UNITED STATES PATENTS

| | | | |
|---|---|---|---|
| 3,453,295 | 7/1969 | Alvarez | 260/397.3 |
| 3,803,183 | 4/1974 | Bacso | 260/397.4 |

*Primary Examiner*—Elbert L. Roberts
*Attorney, Agent, or Firm*—Gerald D. Sharkin; Richard E. Vila; Frederick H. Weinfeldt

[57] ABSTRACT

13-alkyl-17α-propadienylgona-4,9-dien-17β-ol-3-ones and their 17β-oxygenated derivatives are useful in control of fertility and estrus or the menstrual cycle in warm blooded animals.

14 Claims, No Drawings

SUBSTITUTED CARBINOL DERIVATIVES

This is a continuation, of copending application Serial No. 358,345 filed May 8, 1973 (now abandoned) which in turn is a continuation-in-part of copending application U.S. Ser. No. 314,833 filed Dec. 13, 1972 now abandoned which in turn is a division of then copending application Serial No. 71,279 filed Sept. 10, 1970, (now U.S. Pat. No. 3,719,670), which in turn is a continuation-in-part of then copending application 778,777 filed Nov. 25, 1968 (now abandoned).

This invention relates to substituted steroids. More particularly it relates to pharmaceutical compositions containing steroidal 17α-allenyl 17β-carbinol derivatives and to the use thereof.

The substituted carbinols of this invention may be represented by the following structural formula I

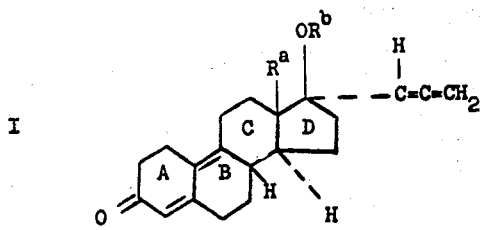

wherein
  $R^a$ is alkyl having 1 to 3 carbon atoms, e.g. methyl, ethyl, n-propyl and isopropyl, and is preferably unbranched; and
  $R^b$ is a hydrogen atom, methyl, acetoacetyl or lower alkanoyl having 2 to 4 carbon atoms, e.g. acetyl, propionyl or butynyl.

The process for preparing compounds of formula (I) where $R^b$ = H, may be represented by the following reaction scheme A:

wherein $R^a$ has the above stated significance, and each of R', R'' and R''' is independently lower alkyl having 1 to 3 carbon atoms, e.g., methyl, ethyl and propyl; methyl being preferred, P is a protected form of rings A, B and C, as indicated below; and Y is halo having an atomic weight of from 35 to 127 or the residue of a sulfonic acid, e.g., Cl, Br, I, mesylate ion, tosylate ion or the like, preferably I.

The organo metallo reagent (IV) has the composition

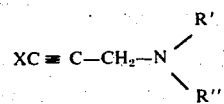

wherein X is an active metal or magnesium bromide or iodide, e.g., Li, K, Na, Al/3, Zn/2, —MgBr, or —MgI, and is prepared by methods disclosed in the literature; and R' and R'' have the above stated significance.

Compound (III) is prepared by treating a corresponding 17-ketosteroid (II) with reagent (IV) in a solvent at a temperature of —30° to 100°C., preferably —20°.to 50°C. followed by standard hydrolysis of the resulting adduct in neutral or basic aqueous medium, e.g., water or saturated ammonium chloride solution. The solvent used is dependent upon the composition of the organo-metallo reagent. For example, if X is MgBr, MgI or Li, the solvent may be ether or tetrahydrofuran, if X is Na, the solvent may be liquid ammonia-ether, liquid ammonia-tetrahydrofuran, dioxane, pyridine or dioxane-pyridine. Particularly advantageous is the use of X=Li in the presence of complexing amines, e.g., ethylene diamine. This process is represented by step $a_1$. The temperature and solvent are not critical.

Compound (V) is prepared by treating compound (III) with compound (VI) in a solvent such as acetone,

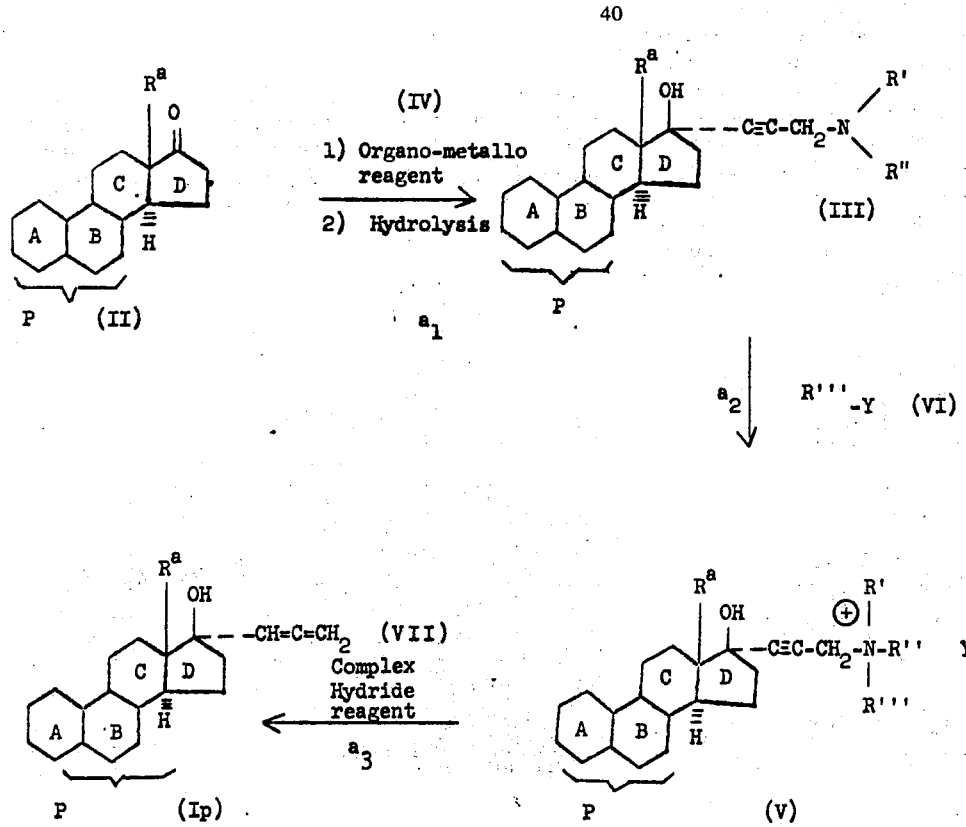

etc., at a temperature of −20°C. to 30°C. This is represented by step $a_2$. The temperature and solvent are not critical.

Compound (Ip) is prepared by treating in a solvent compound (V) with a complex hydride reagent (VII) such as Li Al H$_4$, at a temperature of −80° to 80°C. The solvent may be ether, tetrahydrofuran, pyridine or the like. This is represented by step $a_3$. Again, neither temperature nor solvents are critical.

The compounds of Formula I where $R^b$ is alkanoyl may be obtained using standard methods for acylating a tertiary hydroxy group, e.g., by use of an acylating agent in the presence of a strong acidic catalyst. For example, a compound Ip may be converted into a Compound I where $R^b$=OCOCH$_3$ by use of e.g., acetic anhydride in which calcium hydride had previously been suspended.

The compounds of Formula I where $R^b$ is methyl may be obtained in a manner known per se, for instance by treating a compound Ip at a temperature of about −30°C. to 30°C. with 1–1.2 equivalents of strong base (e.g. NaNH$_2$ or KNH$_2$ in liquid ammonia or LiCH$_3$ in ether) to form a 17-O-anion of compound Ip, and treating the latter, in the same mixture, with 1–50 equivalents of methyl iodide.

Compounds of Formula I wherein $R^b$ is acetoacetyl are obtainable by reacting a compound of Formula I bearing a 17β-hydroxy group with a suitable reagent, e.g., diketene, under conventional conditions employed in carrying out such a reaction. For example, a 17β-hydroxy bearing compound of Formula I may be reacted with diketene in an inert organic solvent, e.g., benzene or toluene or mixture thereof, in the presence of a small amount of organic tertiary amine base, e.g., pyridine, at relatively low temperatures, e.g., at from about −5° to +35°C.

The disclosure below respecting protective groups pertains as well to the above described method for methylating and acylating compounds Ip and III.

Certain compounds of Formula (II) and protected forms thereof are known and may be prepared by methods disclosed in the literature; and those compounds not specifically disclosed may be prepared according to analogous methods from known materials.

Conventional recovery techniques are utilized for obtaining the compounds of Formula (I), e.g., crystallization, column or layer chromatography, etc.

The above-mentioned protected forms P of the steroidal compounds include the structures P1 and P2 embracing rings A, B and C.

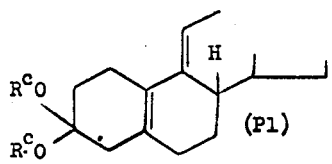
(P1)

and

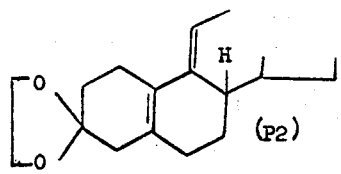
(P2)

wherein $R^c$ is lower alkyl, e.g., being from 1 to 4 carbon atoms, such as methyl, ethyl, propyl or butyl. "Deprotection" can be achieved in conventional ways; i.e., with P1 and P2, hydrolysis in acid medium followed by conjugation of the double bonds in acid or basic medium. The above-described "protected" forms are advantageously retained until compound Ip where $R^b$=H or CH$_3$ is obtained, which compound may then be deprotected as described above to obtain the unprotected form of a compound I where $R^b$=H or CH$_3$. A compound of formula I wherein $R^b$=H can then be converted if desired to a particular compound of Formula I where $R^b$=acyl, by conventional means.

In accordance with an additional aspect of this invention the compounds of Formula III may be prepared by the following Reaction Scheme B, wherein $R^a$, R', R" and P are as defined above.

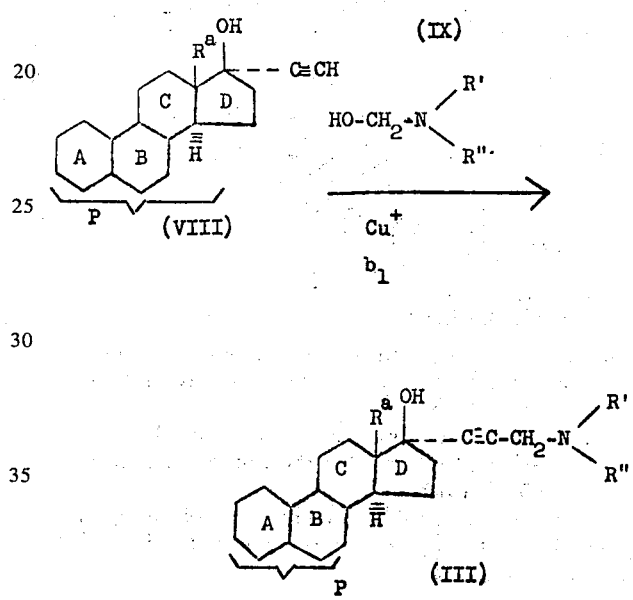

In this scheme, step $b_1$ is a Mannich-type reaction involving the ethynyl group in VIII; it can be carried out under conditions known to be operative in Mannich reactions of this type. Preferably, however, step $b_1$ is carried out with geminal amino alcohols of the type

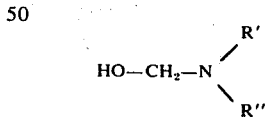

(R' and R" being as defined above) in the presence of Cu$^+$ ions and small amounts of weak acid, (e.g., acetic acid), at temperatures of 10° to 80°C., preferably from about 50° to 70°C. in an inert solvent, such as dioxane and tetrahydrofuran.

In the above-described procedures, the starting materials and reagents are known and may be prepared by methods described in the literature, or where not known may be prepared in a manner analogous to that for preparing the known compounds.

An advantageous alternative method of preparing a Compound I in which $R^b$ is a hydrogen atom, i.e. a Compound Ia is a multi-step procedure which may be conveniently represented by Reaction Scheme C, below, in which $R^a$ is as defined above, and
either $R^1$ and $R^2$, which may be the same or different, each signify an alkyl radical of 1 to 3 carbon atoms,
or $R^1$ and $R^2$, together with the nitrogen atom to which they are attached, form a pyrrolidino, piperidino, or homopiperidino radical,
$R^3$ signifies an alkyl radical of 1 to 3 carbon atoms; and
$X^\ominus$ signifies the anionic residue of a mineral or organic sulphonic acid, other than a fluoride ion;
(alkyl radical suitable as $R^1$, $R^2$ and $R^3$ are understood as including methyl, ethyl, n-propyl and isopropyl radicals, but preferably being unbranched):

REACTION SCHEME C

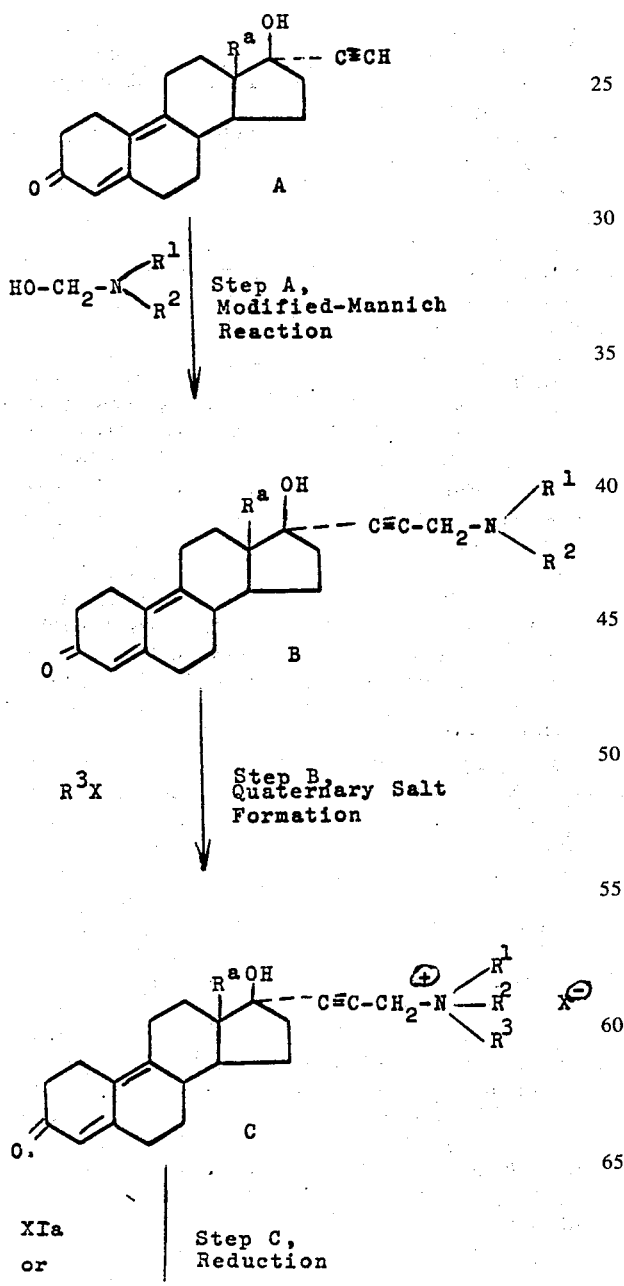
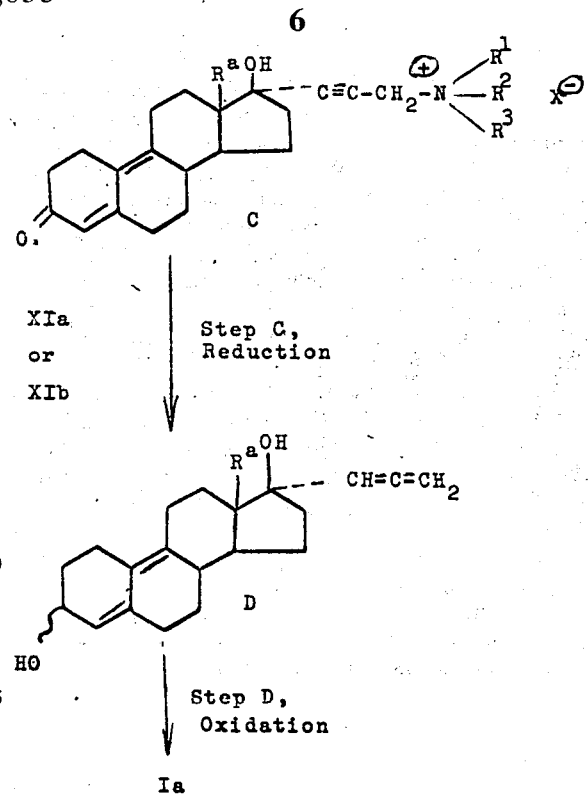
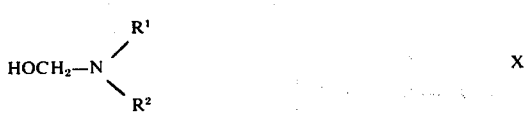

With respect to Reaction Scheme C, above, it will be noted that compounds A are unprotected forms of Compounds VIII of Reaction Scheme B, and that whereas step $b^1$ is a conventional Mannich reaction, Step A employs a modified Mannich reaction. Accordingly, Compounds of formula B are obtained by treating by a Mannich-type reaction (Step A) a 17α-ethynyl 17β-hydroxy-steroid of the formula A with an aminomethanol, i.e. a compound of formula X $$HOCH_2-N\diagdown_{R^2}^{R^1} \qquad\qquad X$$

in which $R^1$ and $R^2$ are as defined above, in the presence of a monovalent coinage metal ion, i.e., Cu(I), Au(I) or Ag, preferably Cu(I). Step A is conveniently carried out at a temperature of from 20° to 80°C., preferably from 20° to 30°C. The reaction may be carried out in a solvent, e.g. in an ether such as diethylether, tetrahydrofuran or p-dioxane, and in the presence of a salt, adduct or complex of copper, silver or gold capable of providing monovalent ions under the reaction conditions. As Examples of suitable salts may be given cuprous chloride, cuprous bromide, cuprous nitrate, cuprous acetate, silver or gold (I) chloride or bromide, or silver nitrate; cuprous chloride being preferred. As Examples of complexes may be given copper, silver and gold cyanides. Where any of the reactants is liquid under the reaction conditions, such may be used in excess to serve as reaction medium. A preferred solvent is p-dioxane. A preferred Compound X is dimethylaminomethanol.

Compounds of formula C are obtainable by quaternization (Step B) of a 17α-dialkylaminopropynyl bearing steroid, i.e., a compound of formula B, with a compound of the formula
$R^3X$ in which $R^3$ and X are as defined above. Step B, the quaternization, may be carried out in conventional manner for preparing a quaternary ammonium salt from a tertiary amine. A suitable reaction temperature is from −20° to 100°C. Where a compound of formula $R^3X$ is liquid under the reaction conditions, such may be used in excess to serve as reaction medium. Alternatively, a solvent, such as acetone or acetonitrile may be used. Ions suitable as X include a monovalent ion of a halogen atom having an atomic weight of from 34 to 128; i.e., chloro, bromo, or iodo, or the residue of a sulfonic acid, e.g. of an alkylsulfonic acid such as a mesylate ion, or of an aromatic sulfonic acid, such as a tosylate ion, or the like. Preferred compounds of formula $R^3X$ are methyl iodide and methyl p-toluenesulphonate. Thus, it is particularly preferred that reagents be used such that each of $R^1$, $R^2$ and $R^3$ is methyl and X is iodo.

In Step C of Reaction Scheme C, compounds of formula D are obtained by reducing a compound of formula C. The reduction may be carried out by use of a complex metal hydride, using a hydride ion source selected from compounds of formula XIa

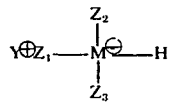

in which Y signifies an alkali or alkaline earth metal,
M signifies aluminum, or gallium, and
$Z_1$, $Z_2$ and $Z_3$, which may be the same or different, each signify a hydrogen atom, an alkyl or alkoxy radical of 1 to 6 carbon atoms or an alkoxyalkoxy radical wherein the alkyl portion has from 1 to 6 carbon atoms and alkylene portion has from 2 to 6 carbon atoms,
and compounds of formula XIb

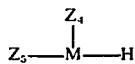

in which M is as defined above, and
$Z_4$ and $Z_5$, which may be the same or different, each signify a hydrogen atom or an alkyl radical of 1 to 6 carbon atoms,
in an aprotic medium not detrimental to the reaction.

The alkyl and alkoxy radicals mentioned above in connection with Compounds of formulas XIa and XIb are understood to include as the alkyl portion thereof methyl, ethyl, propyl, butyl, amyl and hexyl, including isomers where such exist, but are preferably unbranched; and the alkylene radicals are understood to include ethylene, n-propylene, n-butylene, n-amylene and n-hexylene radicals.

In Step C, the aprotic medium may, for example, be an ether, such as diethyl ether, tetrahydrofuran or dioxane, or an aromatic compound such as benzene, toluene or pyridine. The medium may be a single material or a mixture. A suitable reaction temperature is from −40° to +120°C., e.g. the boiling temperature of the reaction mixture. Preferred reaction temperatures, however, are from −10° to +50°C. Whilst higher temperatures result in faster reaction rates, lower temperatures tend to give purer products. It is preferable to exclude moisture from the reaction mixture.

As representative of hydride ion sources may be given lithium aluminium hydride, sodium dihydro bis-(2-methoxy ethoxy) aluminate, lithium gallium hydride, magnesium aluminium hydride, lithium diisobutylmethyl aluminium hydride, lithium trimethoxy aluminium hydride and diethyl aluminium hydride, lithium aluminium hydride and sodium dihydro bis-(2-methoxy ethoxy) aluminate being preferred. In the formula XIa, given above, although, as will be appreciated, alkaline earth metals are divalent, $Y^+$ has, for the sake of simplicity, been shown as monovalent. As examples of significances of Y may be given lithium, potassium, calcium and magnesium.

In Step D, Compounds Ia are obtained by oxidation of the 3-hydroxy function of a compound of formula D. The oxidation may be carried out in conventional manner. Suitable oxidizing agents include quinones, such as p-benzoquinone, chloranil or 2,3-dichloro-5,6-dicyanobenzoquinone, (DDQ) and activated manganese dioxide, preferably 2,3-dicyano-5,6-dichlorobenzoquinone. The oxidation is preferably carried out at a temperature of from 10° to 50°C., more preferably from 20° to 30°C. Preferably an inert solvent, e.g. a cyclic ether such as dioxane, or a tertiary alkanol such as t-butanol, is employed.

Compounds of formula D employed in Step D are mixtures of $3\alpha,17\beta$-diols and $3\beta,17\beta$-diols. Such a mixture results from the reduction of the 3-oxo function of a compound of formula C during Step C. In Step D the 3-hydroxy function of a compound of formula D is oxidized to an oxo function regardless of its isomeric configuration. Hence the proportion of $3\alpha$- to $3\beta$-hydroxy isomers constituting a compound of formula II employed in Step D is unimportant.

Reagents and starting materials used in the abovedescribed processes, e.g. compound of formulae II, IV, VI, VII, VIII, IX, X, $R^3X$, XIa, XIb and A are known and may be prepared by methods described in the literature, or where not known, may be prepared by methods analogous to those for preparing the known compounds. Many of these compounds are obtainable commercially.

Alternative to the process of Reaction Scheme C, described above, there may be used as starting material, a 3-hydroxy analog of a Compound of formula A, in place of a Compound of formula A, and by applying the method of each of Steps A and B obtain the 3-hydroxy analogs of compounds of formulae B and C, respectively. The product obtained by applying the method of Step C to a 3-hydroxy analog of a Compound of formula C will, however, be the same as a Compound of formula D, albeit the ratio of $3\alpha$- to $3\beta$-hydroxy isomers may vary. This, however, is unimportant, as noted above, and the desired compound of formula Ia can then be obtained by application of Step D. If desired, when using a 3-hydroxy analog of the Compound of formula A, Step A can be carried out using in place of the conditions of the modified Mannich reaction described above in connection with Reaction Scheme C, the conventional Mannich reaction conditions described in connection with step $b_1$ of Reaction Scheme B. In addition, if so desired, the abovedescribed modified Mannich reaction technique may be applied to carry out step $b_1$ (in the procedure of Reaction Scheme B) to obtain Compounds of formula III as such technique is applicable to 3-oxo steroidal compounds whether in protected or unprotected form.

The substituted carbinol derivatives represented by formula (I) above are useful because they possess pharmacological properties in animals. In particular, such compounds are useful as agents in the control of fertility including the control and regulation of estrus or the menstrual function in warm-blooded animals, as they possess progestational activity as indicated by standard tests, such as the clauberg test, e.g. the method basically described in Endocrinology 63 (1958) 464 wherein the rabbit is given from 0.0025 to 1.0 milligram of active agent.

These compounds may be combined with a pharmaceutically acceptable carrier or adjuvant. They may be administered orally or parenterally. The dosage will vary depending upon known factors such as the mode of administration utilized and the particular compound employed. However, in general, satisfactory results are obtained in warm-blooded animals, i.e. birds and mammals, when the compounds are administered at a daily dosage of from about 0.0025 milligram to 50 milligrams, e.g. from about 0.01 milligram to 2 milligrams. It will be appreciated by those skilled in the art that the daily dosage level is not directly related to body weight. Dosage forms suitable for internal administration comprise from about 0.0025 milligram to 50 milligrams, e.g. from about 0.005 milligram to about 2 milligrams, of the compound in admixture with a solid or liquid pharmaceutical carrier or diluent, solid forms, e.g. tablets and capsules, being preferred.

As noted above, the compounds of formula I are also useful as agents in the control and regulation of the menstrual or estrus function. For such uses, compounds of formula (I) may be administered alone in the manner and dosage described above, or in combination with a suitable estrogenic agent, the latter, for example at a dosage of about 0.1 milligram. For the regulation of the menstrual function, the estrogenic agent may be admixed with a compound of formula I; or, alternatively, the estrogenic agent may be administered alone in the first part of the menstrual cycle and in admixture with the compound of formula I in the latter days of the cycle of the host, i.e. a higher primate.

The compounds 17α-propadienylestra-4,9-dien-17β-ol-3-one, 17β-acetoacetoxy-17α-propadienylestra-4,9-dien-3-one and 17β-acetoxy, 17α-propadienylestra-4,9-dien-3-one are particularly useful as fertility control agents as they have in addition to their progestational activity, estrogenic activity as well as estrogen-antagonistic activity when administered orally or parenterally at daily dosages of from about 0.025 milligram to 30 milligrams, e.g. from about 0.1 milligram to 0.5 milligram. It will be readily appreciated by those skilled in the art that compounds concurrently exhibiting the three above-mentioned properties are highly desirable as they can be used to obtain efficient fertility control at advantageously low dosage levels and thereby minimizes undesirable side-effects commonly associated with standard fertility control agents, e.g. those which comprise an estrogenic agent with a progestational agent.

The three above-mentioned activities can be observed in the white rat by standard test methods; e.g. the progestational activity can be demonstrated by the rat deciduoma method described by Yochim and DeFeo (Endocrinology 71:134, 1962), the estrogenic activity can be demonstrated by observation of cornification of vaginal epithelium of adult female ovariectomized white rats, e.g. by the method of Biggers and Claringbold, and estrogen-antagonistic activity can be demonstrated by observation of inhibition of cornification of vaginal epithelium of adult ovariectomized female white rats caused by standard estrogens.

For example, Compounds I, as particularly represented by 17α-propadienylestra-4,9-dien-17β-ol-3-one, are especially useful in estrus regulation in swine at daily doses more suitably of from about 3 to 30 milligrams, preferably about 4 to 15 milligrams, based on the observation that cystic follicles are not formed. This property is particularly surprising in view of the fact that the formation of cystic follicles is a common result in attempts to regulate estrus in swine with other steriods.

This invention is illustrated but not limited by the following examples, wherein all temperatures are Centragrade, and room temperature is 20° to 30°C., unless indicated otherwise.

EXAMPLE 1

17α-Propadienylestra-4,9-dien-17β-ol-3-one

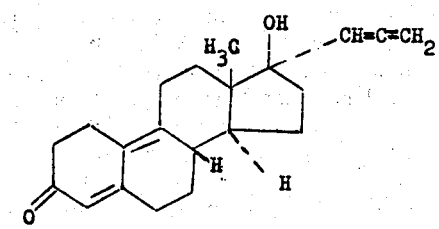

Step 1

17α-Dimethylaminopropynyl-3-ethylenedioxyestra-5(10),9(11)-dien-17β-ol.

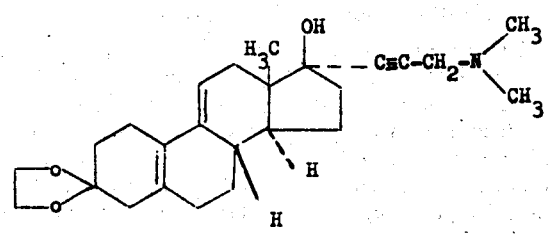

To a Grignard mixture, prepared from 1.50 g. of magnesium, 4.68 g. of ethyl bromide and 70 ml. of tetrahydrofuran, there is dropwise added 5.3 g. of dimethylaminopropyne, dissolved in 10 ml. of tetrahydrofuran. After the evolution of ethaneceases, a solution of 1.888 g. of 3-ethylenedioxyestra-5(10),9(11)-dien-17-one in 30 ml. of tetrahydrofuran is dropwise added, the temperature being maintained at 0°–5°C. during the addition and 20°–25° for 4 further hours. Aqueous 2 N NaOH solution (100 ml.) is added and the mixture concentrated in vacuo at temperatures not exceeding 30°C. until the total volume is 100 ml. The concentrated mixture is then extracted with ether (5 × 25 ml.), using a centrifuge to facilitate separation from the salt-containing aqueous phase. The product* of this step (1) (a₁) is obtained by evaporating the dried ethereal solutions and pumping off any excess dimethylaminopropyne present.

*The product may alternatively be designated, 17α-(3'-dimethylamino-prop-1'-yn-1'-yl)-estra-4,9-dien-17β-ol-3-one.

Step 2

17α-Dimethylaminopropynyl-3-ethylenedioxyestra-5(10),9(11)-dien-17β-ol Methiodide 2 g. of 17α-dimethylaminopropynyl-3-ethylenedioxyestra-5(10),9(11)-dien-17β-ol (product of step 1) is dissolved in 30 ml. of acetone. After addition of 3.2 g. of methyl iodide, the mixture is kept at 8° for 18 hours. The title product of this step (2) crystallizes and is isolated by filtration and washing with anhydrous ether.

Step 3

3-Ethylenedioxy-17α-propadienylestra-5(10),9(11)-dien-17β-ol

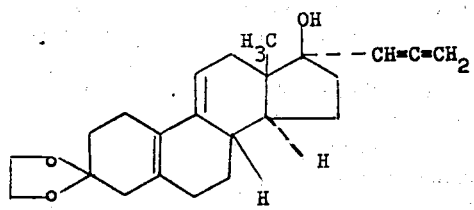

To a suspension of 2.75 g. of the methiodide of step 2, in 50 ml. of tetrahydrofuran, there is added, at −75°, 9.3 ml. of a 0.525 molar lithium aluminum hydride-tetrahydrofuran solution. The mixture is brought to −10° where it is stirred until (~90 minutes) a clear solution is obtained. Finally it is kept at room temperature for 12 hours. 100 ml. of 2 N aqueous NaOH solution containing 50 mg. ditert.-butylcresol is added and the mixture concentrated in vacuo until the total volume is 100 ml. Extraction with 5 × 20 ml. ether on the centrifuge, drying the ethereal solutions over K$_2$CO$_3$ and evaporation gives the title product, 3-ethylenedioxy-17α-propadienylestra-5(10),9(11)-dien-17β-ol.

Step 4

17α-Propadienylestra-4,9-dien-17β-ol-3-one

3 G. of the product of step 3, i.e., 3-ethylenedioxy-17α-propadienylestra-5(10),9(11)-dien-17β-ol is dissolved in a mixture of 25 ml. of methanol and 0.8 ml. of 11 N aqueous hydrochloric acid and is kept at 30°C. for 30 minutes. After dilution with 50 ml. of water, the product is extracted with methylene chloride (5 × 8 ml.). Evaporation of the dried methylene chloride solutions, followed by recrystallization of the residue from methanol yields the title compound, 17α-propadienylestra-4,9-17β-ol-3-one.

Following the procedure of this example but using in place of the 3-ethylenedioxyestra-5(10),9(11)-dien-17-one starting material an equivalent amount of
 a. 13-Ethyl- 3-ethylenedioxygona-5(10),9(11)-dien-17-one; or
 b. 3-ethylenedioxy-13-n-propylgona-5(10),9(11)-dien-17-one, there is obtained:
 a. 13-Ethyl-17α-propadienylgona-4,9-dien-17β-ol-3-one; or
 b. 17α-propadienyl-13-n-propylgona-4,9-dien-17β-ol-3-one.

EXAMPLE 2

17α-Propadienylestra-4,9-dien-17β-ol-3-one

Step 1

17α-Dimethylaminopropynyl-3-ethylenedioxyestra-5(10),9(11)-dien-17β-ol

To a solution of 2.5 g. of 3-ethylenedioxy-17α-ethynylestra-5,(10),9(11)-dien-17β-ol in 25 ml. of dioxane, is added 2.5 ml. of dimethyl-amino methanol, 80 mg. of cuprous chloride and 1.4 ml. of glacial acetic acid. The stirred reaction mixture is then maintained at a temperature of 60 to 70° for 2½ hours and then cooled and diluted with ice/water containing sufficient sodium bicarbonate to insure that the solution remains basic. The organic material is extracted with methylene chloride and the solution so obtained dried over sulfate and evaporated. The residue is crystallized from acetone-petroleum ether (b.p.60–90°); 1/1, to yield 17α-dimethylaminopropynyl-3-ethylenedioxyestra-5(10),9,(11)-dien-17β-ol, m.p. 161–163°.

Step 2

Methiodide Salt

To a solution of 2.6 g. 17α-dimethylaminopropynyl-3-ethylenedioxy-estra- 5(10),9(11)-dien-17β-ol in 70 ml. of acetone is added 20 ml of methyl iodide. The solution is kept at a temperature of 5° for 18 hours and then the solvent removed and the residue is crystallized from acetone to yield the product, i.e., the methiodide salt of 17α-dimethylaminopropynyl-3-ethylenedioxyestra-5(10),9(11)-dien-17β-ol, m.p. 229°230°.

Step 3

3-Ethylenedioxy-17α-propadienylestra-5(10),9(11)-dien-17β-ol

To a suspension of 3.2 g. of the methiodide salt (prepared in Step 2), in 100 ml. of anhydrous tetrahydrofuran under ice cooling is added dropwise 16 ml. of a 0.85 M solution of lithium aluminum hydride in tetrahydrofuran. The reaction mixture is allowed to warm to room temperature and stirred for a total of 1½ hours by which time solution is almost complete. Water is then added under cooling to decompose the excess hydride reagent, and on continued addition of water, a solid precipitates. This is isolated and dissolved in methylene dichloride. The organic solution is dried over sodium sulfate evaporated to yield 3-ethylenedioxy-17α-propadienylestra-5(10),9(11)-dien-17β-ol.

Step 4

17α-Propadienylestra-4,9-dien-17β-ol-3-one

Using the product of Step 3, above and repeating the procedure described in Step 4 of Example 1, yields the title compound, 17α-propadienylestra-4,9-dien-17β-ol-3-one.

EXAMPLE 3

17α-Dimethylaminopropynyl-3-ethylenedioxyestra-5(10),9(11)-dien-17β-ol

A total of 5.2 g. of lithium is added portionwise to 500 ml of ethylenediamine stirred and maintained at a temperature of 50–60° under nitrogen. After the addition is complete, the resulting blue solution is heated to 95° for 1 hour when a pale yellow reaction mixture is obtained which is then cooled to 10° and 58 g. of dimethylaminopropyne is added dropwise over 5 minutes. Stirring is continued at room temperature for 1 hour, when a solution of 11 g. of 3-ethylenedioxyestra-5(10),9(11)- dien-17-one in 150 ml. of tetrahydrofuran is added. The mixture is now stirred at room temperature for 24 hours. After cooling (ice-water), 1000 ml. of saturated aqueous sodium chloride are added and the resulting organic layer is separated. After drying over sodium sulfate, the solvent is removed and the residue is crystallized from acetone/pet. ether, 1/1, to yield 17α-dimethylaminopropynyl-3-ethylenedioxyestra-5(10),9,(11)-dien- 17β-ol, m.p. 161°–163°.

The thus-obtained intermediate compound may be utilized in the same manner as the product obtained in Step 1 of Example 2 to obtain 17α-propadienylestra-4,9-dien-17β-ol-3-one.

EXAMPLE 4

17β-Acetoacetoxy-17α-propadienylestra-4,9-dien-3-one

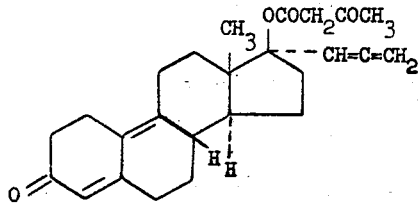

To a solution of 1.0 g. of 17α-propadienylestra-4,9-dien-17β-ol-3-one in a mixture of 18.5 ml. of benzene, 9.25 ml. of toluene and 0.23 ml. of pyridine, there is dropwise added, at 0°, 1.8 ml. of diketene, dissolved in 9 ml. of benzene. The mixture is then kept at 25° for 3 hours. The product is isolated by washing the mixture with ice-cold 0.1 N sodium hydroxide and water, drying over anhydrous sodium sulfate, evaporating to dryness and purifying the oil thus obtained by chromatoplate techniques (silica gel S development: $CHCL_3$-MeOH 98/2): $[\alpha]_D = -245.0$ (C=1, $CHCL_3$).

EXAMPLE 5

17β-Acetoxy-17α-propadienylestra-4,9-dien-3-one

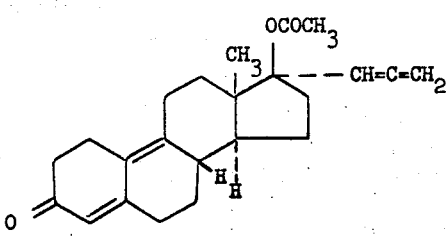

A mixture of 0.050 g. of calcium hydride in 5 ml. of acetic anhydride is refluxed for 1 hour then 0.5 g. of 17α-propadienylestra-4,9-dien-17β-cl-3-one is added and refluxing continued for 3 more hours. After cooling, the mixture is poured on ice and extracted with methylene chloride. The methylene chloride solution is washed with aqueous saturated sodium bicarbonate and then water, dried over anhydrous sodium sulfate and evaporated to give the oily product which is further purified by thin layer chromatography on silica gel (chloroform-methanol: 98/2). $[\alpha]_D = -233.4$ (C=1, $CHCL_3$).

EXAMPLE 6

17β-Methoxy-17α-propadienylestra-4,9-dien-3-one

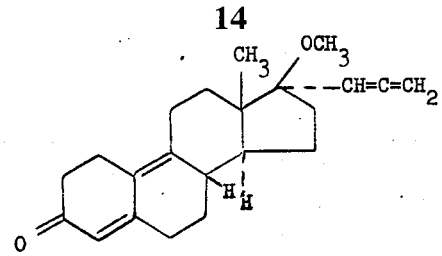

Step 1

3,3-Dimethoxy-17α-propadienylestra-,5(10),9(11)-dien-17β-ol.

Repeating Steps 1, 2 and 3 of Example 1, but using 3,3-dimethoxy-17α-ethynylestra-5(10), 9(11)-dien-17-one in place of the 3-ethylenedioxyestra-5(10), 9(11)-dien-17-one used therein, there is obtained analogously 3,3-dimethoxy-17α-propadienylestra-5(10),9(11)- dien-17β-ol.

Step 2

3,3,17β-trimethoxy-17α-propadienylestra-5(10), 9(11)-diene

To a solution of lithium amide in liquid ammonia (prepared from 73.5 mg. Li and 26 ml of $NH_3$) there is added a solution of 3.55 g of 3,3-dimethoxy-17α-propadienylestra- 5(10), 9(11)-dien-17β-ol in 50 ml of ether. After 2 hours at refluxing ammonia temperature, 2.5 g of methyl iodide is added and the ammonia allowed to escape. Addition of 50 ml of water and separation of the ether phase (and ether washup) followed by the evaporation of the dried ethereal solutions yields the title compound, 3,3,17β-trimethoxy-17α-propadienylestra-5(10), 9(11)- diene.

Step 3

17β-Methoxy-17α-propadienylestra-4,9-dien-3-one

Treating the product of step 2, above, by the procedure of step 4 of Example 1 yields the title product, 17β-methoxy-17α-propadienylestra-4,9-dien-3-one.

EXAMPLE 7

A representative formulation suitable for oral administration is a tablet prepared by standard tabletting techniques which contain the following:

| Ingredients | Part by Weight |
|---|---|
| 17α-Propadienylestra-4,9-dien-17β-ol-3-one | .05 |
| Tragacanth | 2 |
| Lactose | 89.45 |
| Corn starch | 5 |
| Talcum | 3 |
| Magnesium stearate | 0.50 |

EXAMPLE 8

Tablets and capsules containing the ingredients indicated below may be prepared by conventional techniques and are useful in controlling fertility and regulating the menstrual function in the manner described above given daily to a host.

| Ingredients | Weight (mg.) | |
|---|---|---|
| | (a) Tablet | (b) Capsule |
| 17α-Propadienylestra-4,9-dien-17β-ol-3-one | 0.5 | 0.5 |
| Tragacanth | 10 | — |
| Lactose | 247.0 | 299.5 |
| Corn starch | 25 | — |
| Talcum | 15 | — |
| Mangesium stearate | 2.5 | — |
| Total | 300.0 mg. | 300.0 mg. |

EXAMPLE 9

Tablets and capsules containing the ingredients indicated below may be prepared by conventional techniques and are useful in controlling fertility and controlling and regulating estrus in large domestic mammals in the manner described above given daily to said host.

| Ingredients | Weight (mg.) | | |
|---|---|---|---|
| | (a) Tablet | (b) Capsule | (c) Capsule |
| 17α-propadienylestra-4,9-dien-17β-ol-3-one | 6 | 6 | 10 |
| Tragacanth | 10 | — | — |
| Lactose | 241.5 | 294 | 490 |
| Corn Starch | 25 | — | — |
| Talcum | 15 | — | — |
| Mangesium stearate | 2.5 | — | — |
| Total | 300.0 mg. | 300 mg. | 500 mg. |

EXAMPLE 10

The following pharmaceutical composition is formulated with the indicated amount of active agent using conventional techniques. The injectable suspension represents a formulation useful in controlling fertility in the manner described above given daily to a host.

| Ingredients | Weight % |
|---|---|
| 17α-Propadienylestra-4,9-dien-17β-ol-3-one | 1.0 |
| Sodium alginate | 0.5 |
| Lecithin | 0.5 |
| Sodium chloride | as desired |
| Buffer agent to adjust pH for desired stability | as desired |
| Water | to desired volume |

EXAMPLE 11

17α-propadienylestra-4,9-dien-17β-ol-3-one.

Step A.

17α-(3'-dimethylamino-prop-1'-yn-1'-yl)-estra- 4,9-dien-17β-ol-3-one.

326 g. of 17α-ethynylestra-4,9-dien-17β-ol-3-one is dissolved in 3.26 liters of p-dioxane, and 29 g. of cuprous chloride then added thereto and stirred for 5 minutes at room temperature. 290 Ml. of dimethylaminomethanol is then added and the mixture stirred for 45 minutes. While stirring is continued, 12 liters of water is slowly added. 6 liters of saturated aqueous sodium chloride solution is then added and stirring continued for 30 minutes, resulting in separation of the reaction product as crystals. The crystalline product is recovered by filtration, washed with 5 liters of water, then dried under vacuum, to obtain 17α-(3'-dimethylamino-prop-1'-yn-1'-yl) 4,9-dien-17β-ol-3-one, m.p. 147°–151°C.

Step B.

17α-(3'-dimethylamino-prop-1'-yn-1'-yl)-estra-4,9-dien-17β-ol-3-one methyl iodide.

To 375.5 g. of the product of Step A, above, is added 6 liters of acetone and the mixture stirred for 30 minutes at 40°. 50 g. of celite (diatomaceous earth) is then added. While warm, the mixture is filtered, and the filter cake washed with 600 ml. of acetone. The combined filtrate and wash are cooled to room temperature, then 106 ml. of methyl iodide is added thereto with stirring, and stirring is continued for 30 minutes. With stirring, 7 liters of diethyl ether are then added. The mixture is then cooled in an ice bath with stirring for 30 minutes, resulting in separation of the product as crystals, which are recovered by filtration. The crystalline product is washed with 1 liter of diethyl ether, and then dried at room temperature under vacuum to obtain the title methyl iodide salt, m.p. 213°to 215° (which should be protected from light).

Step C.

17α-propadienylestra-4,9-diene-3,17β-diol

A suspension is formed by mixing 480 g. of the product of Step B with 14.4 liters of dry tetrahydrofuran (THF) with vigorous stirring. 600 ml. of a 70% benzene solution of sodium bis(2-methoxyethoxy) aluminum hydride* (w/v) is diluted with dry THF to 1200 ml. and is added to the stirred suspension over a period of 30 minutes at room temperature. Stirring is then continued for 6 hours. With vigorous stirring, 575 ml. of water is slowly added to the reaction mixture, so that the temperature does not rise above 35°. Stirring is then continued for 3 hours. 100 g. of celite is then added to the reaction mixture which is then filtered, and the filter cake washed with 3 liters of THF. The combined filtrate and wash are then neutralized with glacial acetic acid (about 200 ml.) The neutralized solution is then concentrated under vacuum, displacing the THF with 5 liters of methyl isobutyl ketone (MIBK). The MIBK solution is washed first with 700 ml. water containing 10 g. of sodium thiosulfate, then with 700 ml. of water, and then twice with 500 ml. portions of saturated aqueous sodium chloride solution. The MIBK solution is then concentrated to a syrup under vacuum, and then maintained under high vacuum to remove residual solvents to obtain 17α-propadienylestra-4,9-dien-3,17β-diol as a yellow syrup.

*Also called sodium dihydro bis-(2-methoxyethoxy) aluminate.

Step D.

17α-propadienylestra-4,9-dien-17β-ol-3-one.

311 g. of the product of Step C are dissolved in 3.2 liters of p-dioxane, and 1300 ml. of a solution of 255 g. of 2,3-dichloro-5,6-dicyanobenzoquinone (DDQ) in p-dioxane, is slowly added thereto, with stirring, so that the temperature does not rise above 35°. Stirring is then continued at room temperature for 1.5 hours, resulting in the separation of a crystalline material. The crystalline material is collected on a filter, and washed with 500 ml. of p-dioxane. The filtrate and wash are combined and, with stirring, 1.5 liters of an aqueous solution of 36.0 g. of sodium hydrosulfite and 76.0 g. of anhydrous potassium carbonate, added thereto. The mixture is then stirred for an additional 15 minutes, and then added to a mixture of 4 liters of saturated aqueous sodium chloride and 6 liters of water. The resulting mixture is then extracted 5 times with 1 liter portions of diethyl ether. The combined ether extracts are washed twice with 1 liter portions of saturated aqueous sodium chloride. The ethereal solution is concentrated, under vacuum, to obtain a syrup, from which residual p-dioxane is removed by high vacuum. The syrup is then dissolved in a minimum amount of diethyl ether, and the resulting solution charged to a column of 600 g. of aluminum oxide. The column is then washed with 4 liters of diethyl ether, which is then concentrated under vacuum to a volume of 1 to 1.5 liters. Crystals of the title product are obtained by cooling the concentrated solution in an ice bath. The crystalline product is recovered by filtration and washed with 300 ml. of an ice-cold mixture of hexane-ether (1:1) to obtain the refined product, m.p. 111° to 113°. Additional product can be recovered from the wash and filtrate, if desired.

What is claimed is:

1. A pharmaceutical composition suitable for internal administration comprising an amount of a compound of the formula

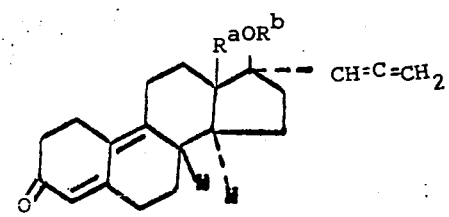

wherein
$R^a$ is alkyl having 1 to 3 carbon atoms; and
$R^b$ is a hydrogen atom, methyl, acetoacetyl or lower alkanoyl having 2 to 4 carbon atoms effective in controlling fertility in a mammal and a pharmaceutical carrier.

2. A composition of claim 1 wherein the carrier is solid.

3. A composition of claim 1 wherein the compound is present in an amount of from about 0.005 milligram to 2 milligrams.

4. A composition of claim 1 wherein the compound is 17α-propadienylestra-4,9-dien-17β-ol-3-one.

5. A composition of claim 4 wherein the compound is present in an amount of from about 0.1 milligram to 0.5 milligram.

6. A method of controlling fertility in a mammal comprising internally administering thereto an amount of a compound of the formula

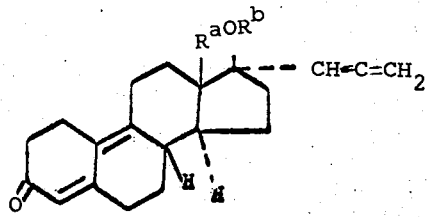

wherein
$R^a$ is alkyl having 1 to 3 carbon atoms; and
$R^b$ is a hydrogen atom, methyl, acetoacetyl or lower alkanoyl having 2 to 4 carbon atoms, effective in controlling fertility in said mammal.

7. A method of claim 6 wherein the compound is 17α-propadienylestra-4,9-dien-17β-ol-3-one.

8. A method of claim 7 wherein the compound is administered orally.

9. A method of claim 8 wherein the compound is administered at a daily dosage of from about 0.1 milligram to 0.5 milligram.

10. A method of regulating estrus in an adult female pig which comprises internally administering thereto from about 3 milligrams to 30 milligrams per day of a compound of the formula

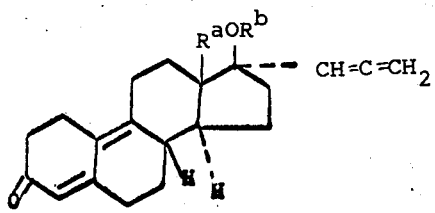

wherein
$R^a$ is alkyl having 1 to 3 carbon atoms; and
$R^b$ is a hydrogen atom, methyl, acetoacetyl or lower alkanoyl having 2 to 4 carbon atoms.

11. A method of claim 10 in which the amount of compound administered is from about 4 milligrams to 15 milligrams per day.

12. A method of claim 11 wherein the compound is 17α-propadienylestra-4,9-dien-17β-ol-3-one.

13. A composition of claim 1 wherein the compound is present in an amount of from about 0.0025 milligram to 50 milligrams.

14. A method of claim 6 wherein the compound is administered in admixture with solid pharmaceutical carrier.

* * * * *